US007375076B2

(12) United States Patent
Lawrence et al.

(10) Patent No.: US 7,375,076 B2
(45) Date of Patent: May 20, 2008

(54) METHODS OF REDUCING VASCULAR PERMEABILITY IN TISSUE BY INHIBITION OF TISSUE PLASMINOGEN ACTIVATOR (TPA) AND TPA INHIBITORS USEFUL THEREIN

(75) Inventors: Daniel A. Lawrence, Derwood, MD (US); Manuel S. Yepes, Rockville, MD (US); Dudley Strickland, Brookeville, MD (US)

(73) Assignee: The Regents of The University of Michigan, Ann Arbor, MI (US)

( * ) Notice: Subject to any disclaimer, the term of this patent is extended or adjusted under 35 U.S.C. 154(b) by 386 days.

(21) Appl. No.: 10/849,540

(22) Filed: May 20, 2004

(65) Prior Publication Data

US 2005/0019329 A1 Jan. 27, 2005

Related U.S. Application Data

(60) Provisional application No. 60/471,727, filed on May 20, 2003.

(51) Int. Cl.
A61K 38/00 (2006.01)

(52) U.S. Cl. .......................................... 514/2
(58) Field of Classification Search ............. None
See application file for complete search history.

(56) References Cited

U.S. PATENT DOCUMENTS

| 3,773,919 | A | | 11/1973 | Boswell et al. |
| 4,485,045 | A | | 11/1984 | Regen |
| 4,544,545 | A | | 10/1985 | Ryan et al. |
| 6,008,020 | A | * | 12/1999 | Hastings et al. ........... 435/69.2 |
| 6,103,498 | A | | 8/2000 | Lawrence et al. |
| 6,191,260 | B1 | | 2/2001 | Hastings et al. |
| 6,489,143 | B1 | | 12/2002 | Lawrence et al. |

FOREIGN PATENT DOCUMENTS

| DE | 32 18 121 A1 | 11/1983 |
| EP | 0 102 324 A2 | 7/1983 |
| EP | 0 133 988 A2 | 8/1984 |
| EP | 0 142 641 B1 | 8/1984 |
| EP | 0 052 322 B1 | 3/1985 |
| EP | 0 143 949 B1 | 6/1985 |
| EP | 0 058 481 B2 | 10/1986 |
| EP | 0 036 676 B2 | 9/1990 |

OTHER PUBLICATIONS

Hastings et al., Neuroserpin, a Brain-associated Inhibitor of Tissue Plasminogen Activator Is Localized Primarily in Neurons, JBC, vol. 272, No. 52, Issue of Dec. 26, 1997 pp. 33062-33067.*
Rudd et al., Thrombolytic therapy causes an increase in vascular permeability that is reversed by 1-deamino-8-D-vasopressin, Circulation. Dec. 1991; vol. 84, No. 6, pp. 2568-2573.*
Thomas H. Bugge et al., "Loss of Fibrinogen Rescues Mice from the Pieiotropic Effects of Plasminogen Deficiency", Cell, vol. 87, pp. 709-719, Nov. 15, 1996.
Stella E. Tsirka et al., "Excitotoxin-induced neuronal degeneration and seizure are mediated by tissue plasminogen activator", Nature, vol. 377, pp. 340-344, Sep. 28, 1995.
Zhuo Qian et al., "Tissue-plasminogen activator is induced as an immediate-early gene during seizure, kindling and long-term potentiation", Nature, vol. 361, pp. 453-457, Feb. 4, 1993.
Nicholas W. Seeds et al., "Tissue Plasminogen Activator Induction in Purkinje Neurons After Cerebellar Motor Learning", Science, vol. 270, pp. 1992-1578, Dec. 22, 1995.
"Tissue Plasminogen Activator for Acute Ischemic Stroke", The New England Journal of Medicine, vol. 333, No. 24, pp. 1581-1587, Dec. 14, 1995.
Yanming F. Wang et al., "Tissue Plasminogen Activator (tPA) Increases Neuronal Damage After Focal Cerebral Ischemia in Wild-Type and tPA-Deficient Mice", Nature Medicine, vol. 4, No. 2, Feb. 1998, pp. 228-231.
N. Nagai et al., "Role of Plasminogen System Components in Focal Cerebral Ischemic Infarction, A Gene Targeting and Gene Transfer Study in Mice", Plasminogen System and Cerebral Infarction, May 11, 1999, pp. 2440-2444.
Manuel Yepes et al., "Neuroserpin reduces cerebral infarct volume and protects neurons from ischemia-induced apoptosis", Hemostasis, Thrombosis & Vascular Biology, Blood, Jul. 15, 2000, vol. 96, No. 2, pp. 569-576.
Paolo Cinelli et al., "Neuroserpin, a Neuroprotective Factor in Focal Ischemic Stroke", Molecular and Cellular Neuroscience 18, pp. 443-457 (2001).
Pamela M. Carroll et al., "The mouse tissue plasminogen activator gene 5' flanking region directs appropriate expression in development and a seizure-enhanced response in the CNS", Development 120, pp. 3173-3183 (1994).
Zhenggang Zhang et al., "Adjuvant Treatment With Neuroserpin Increases the Therapeutic Window for Tissue-Type Plasminogen Activator Administration in a Rat Model of Embolic Stroke", Circulation, Aug. 6, 2002, pp. 740-745.
Toshiaki Aoki Ph.D. et al., "Blood-Brain Barrier Disruption and Matrix Metalloproteinase-9 Expression During Reperfusion Injury Mechanical Versus Embolic Focal Ischemia in Spontaneously Hypertensive Rats", Stroke, Nov. 2002, pp. 2711-2717.

(Continued)

Primary Examiner—Robert B. Mondesi
(74) Attorney, Agent, or Firm—Marshall, Gerstein & Borun LLP

(57) ABSTRACT

The present invention is a method of reducing vascular permeability in tissue of a subject comprising inhibiting the activity of serine proteinase tissue-type plasminogen activator (tPA). This tPA activity which increases permeability of the tissue in a subject results in edema in the tissue is separate from tPA's thrombolytic activity. The present invention more specifically relates to administering an amount of a tPA inhibitor sufficient to reduce the vascular permeability increasing activity of tPA in a subject. Useful tPA inhibitors for the present method are neuroserpin, mutant neuroserpin, wild-type PAI-1, mutant PAI-1, an antibody that binds to tPA, an antibody that binds to the low-density lipoprotein (LDL) receptor or a low-density lipoprotein (LDL) receptor family antagonist.

18 Claims, 3 Drawing Sheets

OTHER PUBLICATIONS

Guojun Bu, "Receptor-associated protein: a specialized chaperone and antagonist for members of the LDL receptor gene family", Current Opinion in Lipidology, vol. 9, No. 2, Apr. 1998, pp. 149-155.

Gary A. Silverman et al., "The Serpins Are an Expanding Superfamily of Structurally Similar but Functionally Diverse Proteins", The Journal of Biological Chemistry, vol. 276, No. 36, Issue of Sep. 7, 2001, pp. 33293-33296.

Jacek Otlewski et al., "Protein Inhibitors of Serine Proteinases", Acta Biochimica Polonica, vol. 46, No. 3, 1999, pp. 531-565.

Robert Langer "Controlled release of macromolecules", Chemtech, Feb. 1982, pp. 98-105.

Deborah A. Eppstein et al., "Biological activity of liposome-encapsulated murine interferon γ is mediated by a cell membrane receptor", Proc. Natl. Acad. Sci. USA, vol. 82, pp. 3688-3692, Jun. 1985.

Karl J. Hwang et al., "Hepatic uptake and degradation of unilamellar sphingomyelin/cholesterol liposomes: A kinetic study", Proc. Natl. Acad. Sci. USA vol. 77, No. 7, pp. 4030-4034, Jul. 1980.

Arti Shukla et al., "Metabolism of D-[$^3$H]threo-1-phenyl-2-decanoylamino-3-morpholino-1-propanol, an inhibitor of glucosylceramide synthesis, an dhte synergistic action of an inhibitor of microsomal monooxygenase", Journal of Lipid Research, vol. 32, 1991, pp. 713-722.

Francis Szoka et al., "Liposomes: Preparation and Characterization", Liposomes: From Physical Structure to Therapeutic Applications, 1981, pp. 51-82.

Francis Szoka Jr. et al., "Procedure for preparation of liposomes with large internal aqueous space and high capture by reverse phase evaporation", Proc. Natl. Acad. Sci. USA, vol. 75, No. 9, pp. 4194-4198, Sep. 1978.

Sarah Netzel-Arnett et al., "Collagen Dissolution by Keratinocytes Requires Cell Surface Plasminogen Activation and Matrix Metalloproteinase Activity", The Journal of Biological Chemistry, vol. 277, No. 47, Nov. 22, 2002, pp. 45154-45161.

Thiennu H. Vu et al., "MMP-9/Gelatinase B is a Key Regulator of Growth Plate Angiogenesis and Apoptosis of Hypertrophic Chondrocytes", Cell., vol. 93, pp. 411-422, May 1, 1998.

Tomoko Betsuyaku et al., "Neutrophil Emigration in the Lungs, Peritoneum, and Skin Does Not Require Gelatinase B", American Journal of Respiratory Cell and Molecular Biology, vol. 20, 1999, p. 1303-1309.

G. Pxaxinos et al., "The Mouse Brain in Stereotaxic Coordinates", Second Edition, Academic Press Inc. San Diego CA (2001).

Olivier Nicole et al., "The proteolytic activity of tissue-plasminogen activator enhances NMDA receptor-mediated signaling", Nature Medicine, vol. 7, No. 1, Jan. 2001, pp. 59-64.

Guojun Bu et al., "Low density lipoprotein receptor-related protein/$\alpha_2$-macroglobulin receptor is an hepatic receptor for tissue-type plasminogen activator", Proc. Natl. Acad. Sci., USA vol. 89, pp. 7427-7431, Aug. 1992.

Chia-Jen Siao et al., "Cell Type-Specific Roles for Tissue Plasminogen Activator Released by Neurons or Microglia after Excitotoxic Injury", The Journal of Neuroscience, Apr. 15, 2003, 23(8):3234-3242.

Philippe Boucher et al., "LRP: Role in Vascular Wall Integrity and Protection from Atherosclerosis", Science, vol. 300, Apr. 11, 2003, pp. 329-332.

Xi Jiang et al., "Storage and Release of Tissue Plasminogen Activator by Sympathetic Axons in Resistance Vessel Walls", Microvascular Research 64, 438-447 (2002).

Vicenta Llorente-Cortès et al., "LDL Receptor-Related Protein Mediates Uptake of Aggregated LDL in Human Vascular Smooth Muscle Cells", Arteriosclerosis, Thrombosis & Vascular Biology, Journal of the American Heart Association, 2000, 1572-1579.

Guojun Bu, "Receptor-associated protein: a specialized chaperone and antagonist for members of the LDL receptor gene family", Current Opinion in Lipidology, vol. 9, No. 2, Apr. 1998, pp. 149-155.

Manuel Yepes et al., "Regulation of seizure spreading by neuroserpin and tissue-type plasminogen activator is plasminogen independent", The Journal of Clinical Investigation, Jun. 2002, vol. 109, No. 12, pp. 1571-1578.

International Search Report of PCT/US04/15873.

Rudd et al., "Thrombolytic Therapy Causes an Increase in Vascular Permeability that is Reversed by 1-Deamino-8-D-Vasopressin", Circulation, vol. 84, No. 6, Dec. 1991, pp. 2568-2573.

Sheng Ye et al., "Serpins & Other Covalent Protease Inhibitors", Proteins, pp. 740-745, 2001.

R. Huber et al., "Implications of the Three-Dimensional Structure of $\alpha_1$-Antitrypsin for Structure and Function of Serpins", Biochemistry, vol. 28, No. 23, Nov. 14, 1989, pp. 8951-8966.

F. Fussi et al., "Aprotinin: Mechanism of Action and Therapeutical Uses", Boll. Chim. Farm., 119 (1980), pp. 631-646.

Claudiu T. Supuran et al., "Bacterial Protease Inhibitors", Medicinal Research Reviews, vol. 22, No. 4, pp. 329-372, 2002.

Jeffrey D. McBride et al., "Synthetic Peptide Mimics of the Bowman-Birk Inhibitor Protein", Current Medicinal Chemistry, 2001, 8, pp. 909-917.

Wolfgang Borth, "$\alpha_2$-Macroglobulin, a multifunctional binding protein with targeting characteristics", The FASEB Journal, vol. 6, No. 15, Dec. 1992, pp. 3345-3353.

Robert R. Rando, "Mechanism-Based Enzyme Inactivators", Pharmacological Reviews, vol. 36, No. 2, pp. 111-142, Jun. 1984.

Torgny Stigbrand et al., "Characterization of Monoclonal Antibodies to Human Tissue-Type Plasminogen Activator: Catalytic Inhibition and One-Two Chain Discriminatory Reactivities", Thrombosis & Haemostasis, 62 (2), pp. 742-747 (1989).

Steingrimur Stefansson et al., "Plasminogen Activator Inhibitor-1 and Vitronectic Promote the Cellular Clearance of Thrombin by Low Density Lipoprotein Receptor-related Proteins 1 and 2", The Journal of Biological Chemistry, vol. 271, No. 14, Apr. 5, 1996, pp. 8215-8220 (1996).

Y. Lazorthes et al., Advances in Drug Delivery Systems and Applications in Neurosurgery, vol. 18, 1991, pp. 144-192.

Ayub Khan Ommaya, "Implantable Devices for Chronic Access and Drug Delivery to the Central Nervous System", Cancer Drug Delivery, vol. 1, No. 2, pp. 169-179, 1984.

Reinhard Pietrowsky et al., "*Brain Potential Changes after Intranasal* vs. *Intravenous Administration of Vasopressin*: Evidence for a Direct Nose-Brain Pathway for Peptide Effects in Humans", Biol. Psychiatry, 1996:39: 332-340.

Kenneth R. Sidman et al., "Controlled Release of Macromolecules and Pharmaceuticals from Synthetic Polypeptides based on Glutamic Acid", Biopolymers, vol. 22, pp. 547-556 (1983).

* cited by examiner

METHODS OF REDUCING VASCULAR PERMEABILITY IN TISSUE BY INHIBITION OF TISSUE PLASMINOGEN ACTIVATOR (TPA) AND TPA INHIBITORS USEFUL THEREIN

RELATED APPLICATIONS

This application claims priority to U.S. provisional application No. 60/471,727 filed on May 20, 2003, the contents of which is incorporated herein by reference.

BACKGROUND OF THE INVENTION

1. Field of the Invention

The present invention relates to a method of reducing vascular permeability in tissue comprising inhibiting the activity of serine proteinase tissue-type plasminogen activator (tPA). This tPA activity which increases permeability of the tissue in a subject results in edema in the tissue is separate from tPA's thrombolytic activity. The present invention more specifically relates to administering an amount of a tPA inhibitor sufficient to reduce the vascular permeability increasing activity of tPA in a subject.

2. Description of the Related Art

Edema is an increase in the extravascular component of the extracellular fluid volume. It may be restricted to some organs, such as the brain (cerebral edema), the peritoneum (ascitis) or the pleura (hydrothorax), or generalized (i.e., anasarca). Edema may result from a variety of pathophysiological events including damage or dysruption of the capillary endothelium with increases in its permeability and transfer of fluids to the extravascular compartment. This type of edema may be observed in patients with cerebral ischemia, head trauma, acute vascular occlusion (i.e., pulmonary embolism), and infection (i.e., sepsis), among others.

More specifically, in conditions in which cerebral edema is associated with pathological conditions, the opening of the blood brain barrier (BBB) results from pathologic increases in cerebrovascular permeability and is associated with the development of vasogenic edema and intracranial hypertension. BBB opening contributes to the morbidity and mortality of patients with many neurological disorders, including head trauma, subarachnoid hemorrhage. Additionally, it is one of the most common complications associated with ischemic stroke Garcia et al., *Acta Neuropathol. (Berl)* 43, 85-95 (1978); Baker et al., *J. Neuropathol. Exp. Neurol.* 30, 668-679 (1971).

Outside of the central nervous system (CNS), tPA is primarily a thrombolytic enzyme and its principal substrate is the zymogen plasminogen. Bugge et al., *Cell* 87, 709-719 (1996). However, within the CNS, tPA is thought to have a very different function, and its activity has been associated with events that require neuronal plasticity, such as long term potentiation and seizures. Tsirka et al., *Nature* 377, 340-344 (1995), Carroll et al., *Development* 120, 3173-3183 (1994), Qian et al., *Nature* 361, 453-457 (1993), Seeds et al., *Science* 270, 1992-1994 (1995), Yepes et al., *J. Clin. Invest* 109, 1571-1578 (2002). As a thrombolytic agent, tPA is the only FDA-approved thrombolytic medication for the treatment of patients with acute ischemic stroke (Tissue plasminogen activator for acute ischemic stroke. The National Institute of Neurological Disorders and Stroke rt-PA Stroke Study Group, *N. Engl. J. Med.* 333, 1581-1587 (1995)). In seeming contradiction, however, animal models of ischemic stroke have shown that both genetic deficiency of tPA (Wang et al., *Nat. Med.* 4, 228-231 (1998), Nagai et al., *Circulation* 99, 2440-2444 (1999)) and inhibition of tPA with its natural inhibitor, neuroserpin (Yepes et al., *Blood* 96, 569-576 (2000), Cinelli et al., *Mol. Cell Neurosci.* 18, 443-457 (2001)), are associated with a significant increase in neuronal survival and a decrease in stroke volume. Consistent with these latter studies, endogenous tPA activity within the CNS increases following middle cerebral artery occlusion (MCAO) (Wang et al., *Nat. Med.* 4, 228-231 (1998), Yepes et al., *Blood* 96, 569-576 (2000)), and thrombolytic treatment with tPA following embolic stroke is associated with evidence of increased vascular permeability (Zhang. et al. *Circulation* 106, 740-745 (2002), Aoki et al. *Stroke* 33, 2711-2717 (2002)). Thus, understanding the mechanisms leading to increased vascular permeability in tissue caused by increased levels of tPA in the affected tissue provides a platform for the development of effective therapeutic strategies aimed at the treatment of patients with pathological conditions associated with increased cerebrovascular permeability and cerebral edema, such as cerebral ischemia, head trauma, stroke and other neurological diseases as well as acute vascular occlusion, such as pulmonary embolism, and infection, such as sepsis.

SUMMARY OF THE INVENTION

The present invention is directed to a method of reducing vascular permeability in tissue of a subject by inhibiting the activity of tPA which is responsible for increasing the permeability of the tissue. More specifically, the activity of tPA that is inhibited is independent of tPA's activity as a plasminogen activator.

The present invention is also directed to a method of reducing vascular permeability in tissue of a subject by inhibiting the vascular permeability increasing activity of tPA by administering to the subject an amount of a tPA inhibitor sufficient to reduce the vascular permeability increasing activity of tPA.

The present invention is further directed to a method of reducing vascular permeability in tissue of a subject by interfering with the interaction of tPA with the low density lipoprotein receptor-related protein (LRP).

The present invention is additionally directed to a method of identifying inhibitors of tPA in tissue wherein the inhibition is measured by a decrease in vascular permeability in the tissue which in turn is a measurement of the vascular permeability activity of tPA. The effect of the inhibitor on the vascular permeability can be measured by comparison to treated and untreated controls.

BRIEF DESCRIPTION OF THE DRAWINGS

FIG. 1A shows the results of an Evans Blue extravasation 6 hours after MCAO and I.V. Evans Blue injection of mouse brains. wt—wild type mouse; Ns—wild type mouse after MCAO followed by intraventricular injection of 2.5 µl of 16 µM recombinant neuroserpin at bregma,—2, medial-lateral:0 and dorso-ventral: 2. Paxinos et al., THE MOUSE BRAIN IN STEREOTAXIC COORDINATES, Academic Press (2001). Ipsilateral—ipsilateral hemisphere of the brain. Contra—contra lateral hemisphere of the brain. tPA$^{-/-}$—tPA deficient. Plg$^{-/-}$—plasminogen deficient. MMP-9$^{-/-}$—MMP-9 deficient (MMP-9=gelatinase B). All images are ipsilateral to the ischemic area except wt-contra, which shows the contralateral hemisphere of the same brain shown in wt-ipsilateral.

FIG. 1B shows the quantitative analysis of Evans Blue extravasation from brain extracts 6 hours after MCAO. The results represent the absorbance of Evans Blue at 620 nm calculated as a percentage of the wild-type control (either C57BL/6J or 129S6/SvEv) as described herein below in the experiments. As a control for the perfusion efficiency, the absorbance of the contralateral hemisphere was subtracted from the hemisphere ipsilateral to the MCAO. For each condition, n=4 and * indicates p<0.05 vs. wild-type. C57 is a wild-type C57BL/6J and C57+Ns is a wild-type C57BL/6J+neuroserpin.

DETAILED DESCRIPTION OF THE PREFERRED EMBODIMENT

Figure 1:
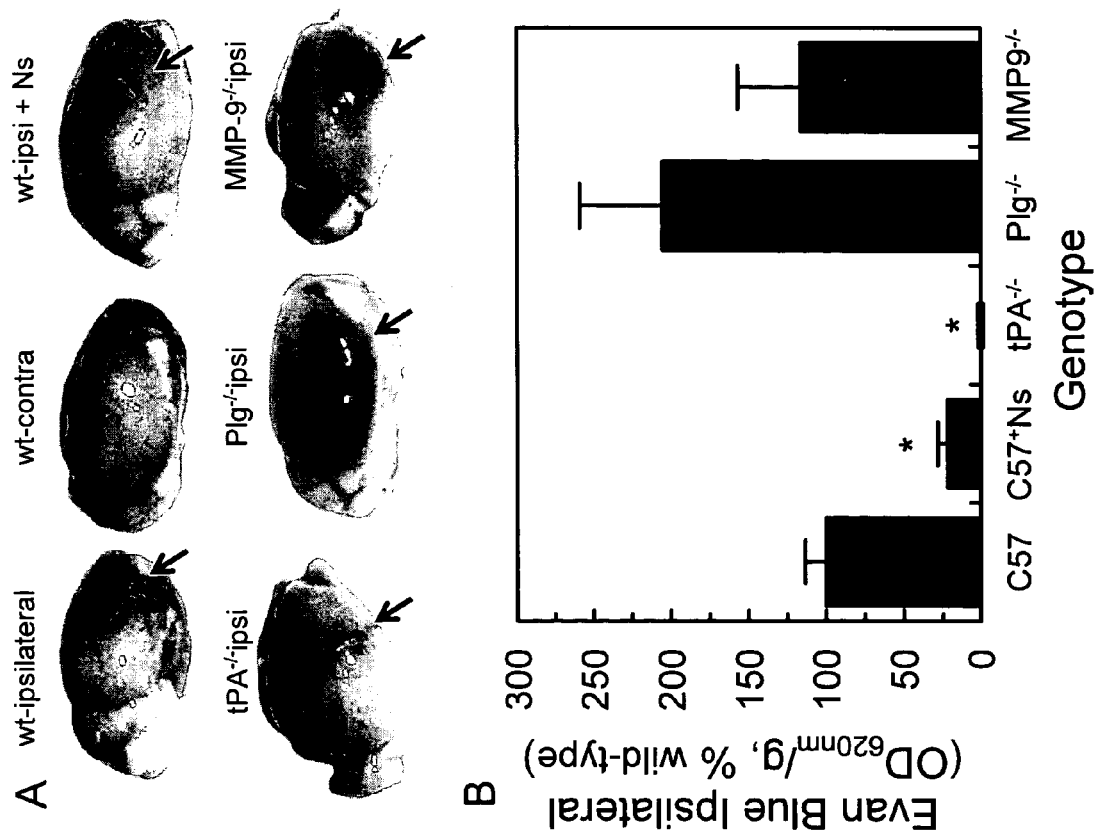
FIG. 1 shows the study of blood brain barrier permeability following cerebral ischemia.

The present inventors have recognized that tPA, acting on the vascular system, is both necessary and sufficient to increase vascular permeability directly, leading to the loss of vascular integrity in tissue, such as blood vessels and the vascular bed. Particularly, tPA within the central nervous system (CNS) directly increases vascular permeability leading to loss of the BBB integrity and results in extravasation of fluids into the interstitial space resulting in edema.

The present invention provides for reducing vascular permeability in tissue by inhibiting tPA, which is responsible for the increase in permeability of the tissue in a subject, which in turn results in edema in and surrounding this tissue. Particularly, the tPA induced increase in vascular permeability can be inhibited by at least two of the following mechanisms: (1) blocking the proteolytic activity of tPA with a proteinase inhibitor or (2) by blocking the binding of tPA to LDL receptor-related protein (LRP) or a related receptor by providing (a) a receptor binding antagonist like receptor associated protein (RAP), (b) an antibody that binds to the LRP or (c) an antibody that binds to tPA. The present inventors have determined that this tPA activity of increasing vascular permeability is independent from tPA's plasminogen activator activity but requires interaction with LRP or another member of the LDL receptor family.

The results presented herein describe a new role for tPA as a regulator of vascular permeability within tissue. The present invention utilizes this information to provide a method for inhibiting tPA's ability to increase vascular permeability, and thereby reducing edema in the surrounding tissue.

The present invention provides a method of reducing vascular permeability in tissue comprising inhibiting the activity of tissue plasminogen activator (tPA) which increases permeability of the tissue in a subject. This tPA activity, which is responsible for the increased permeability of tissue, is independent of its association with the conversion of plasminogen to plasmin.

In one embodiment, the method of inhibiting tPA activity comprises administering to a subject a therapeutically effective amount of a tPA inhibitor to reduce the permeability increasing activity of the tPA in the tissue of the subject. A tPA inhibitor preparation is said to be administered in a "therapeutically effective amount" if the amount administered is physiologically significant. An agent is physiologically significant if its presence results in a detectable change in the physiology of a recipient mammal. In particular, a tPA inhibitor used in the method of the present invention is physiologically significant if its presence reduces permeability of the tissue, which in turn reduces edema in this tissue.

The inventors have recognized that tPA is responsible for the increase in vascular permeability in the tissue resulting in edema in the tissue. Thus, the reduction in tPA's activity results in a reduction in edema in tissue, which may have occurred as a result of an injury, a condition, a disease or a disorder of the subject, wherein the injury, condition, disease or disorder is selected from the group consisting of a head trauma, pulmonary edema, peripheral vascular disease, ischemic stroke, cystitis, pancreatitis, brain tumor, spinal cord tumor, spinal cord trauma, polymyositis, dermatomyositis, pulmonary embolism, enterocolitis, hepatic congestion, cerebral venous thrombosis, intracerebral hemorrhage, post-surgical manipulation, nephritis and glomerulonephritis, brain injury and sepsis. This list of injuries, conditions, diseases and disorders may be expanded to include any injury, condition, disease and disorder that results in swelling or edema in any tissue in the body of a subject.

In one embodiment, the edema is associated with an injury, trauma, disorder or disease to the brain in which increased vascular permeability results in the loss of the integrity of the BBB. Such swelling or edema of the brain may be the result of a head trauma, ischemic stroke, brain tumor, spinal cord tumor or trauma, cerebral venous thrombosis or brain injury. This list of injuries, conditions, diseases and disorders may be expanded to include any injury, condition, disease and disorder that results in swelling or edema to the brain or spinal cord.

To treat the edema associated injury, trauma, disorder or disease, the tPA inhibitor useful in the present method possesses the characteristics to inhibit the permeability increasing activity of the tPA present in the tissue of a subject, and as a result reduces edema in this tissue. For example, useful tPA inhibitors are neuroserpin, mutant neuroserpin, wild-type PAI-1, mutant PAI-1, an antibody that binds to tPA, an antibody that binds to the low-density lipoprotein (LDL) receptor or a low-density lipoprotein (LDL) receptor family antagonist. In one embodiment, the tPA inhibitor is a compound or molecule that inhibits tPA by interfering with the binding or interaction of tPA with a member of the low-density-lipoprotein (LDL) receptor family, for example such as LRP, the LDL receptor-related protein. An example of such an inhibitor is the LDL receptor family antagonist, receptor associated protein (RAP) (Bu et al. *Curr. Opin. Lipidol.* 9, 149-155 (1998)). However, other tPA inhibitors useful for treating edema of tissue surrounding blood vessels and vascular beds may include in one embodiment human neuroserpin, as disclosed in U.S. Pat. No. 6,191,260, wild-type plasminogen activator inhibitor-1 (PAI-1) or a mutant PAI-1 as disclosed in U.S. Pat. No. 6,103,498 or U.S. Pat. No. 6,489,143. But other useful inhibitors of tPA may include but are not limited to PAI-2, PAI-3, protease nexin 1, C1-inhibitor, alpha-1-anti-trypsin, other serpins (serine proteinase inhibitors), Silverman et al., *J. Biol. Chem.,* 276(36):33293-6 (2001), Otlewski et al., *Acta Biochim Pol;* 46(3):531-65 (1999)), Ye et al., *Curr Opin Struct Biol* 11(6):740-5 (2001)), which is a gene superfamily which includes many proteinase inhibitors in blood as well as other proteins with unrelated or unknown functions (see Huber et al., *Biochemistry* (1989) 28:8951-8966), aprotinin, (Fussi, *Boll Chim Farm* 119(11):631-46 (1980)), ecotin and ecotin mutants (Supuran et al., *Med Res Rev;* 22(4):329-72 (2002)), Kazel inhibitors, Kunitz inhibitors, Bowman-Birk inhibitors (McBride et al., *Curr Med Chem,* 8(8):909-17 (2001)); alpha2 macroglobulin, Borth, *FASEB J.* 6(15):3345-53 (1992), chloromethyl ketone inhibitors, heterocyclic isocoumarin inhibitors, mechanism based inhibitors, (Rando, R. R., *Pharmacol Rev* 36(2): 111-42 (1984)) competitive inhibitors of tPA, low-density lipoprotein (LDL) receptor family antagonist, such as the receptor associated protein (RAP), and an antibody that binds to tPA (Stigbrand, T., et al., *Thromb. Haemost.,* 62(2):742-747 (1989)), or an antibody that binds to a low-density lipoprotein (LDL) receptor (Stefansson, S. et al., *J.Biol.Chem.* 271(14):8215-8220 (1996)), such as polyclonal or monoclonal antibodies, that are murine, chimeric, humanized or human antibodies, prepared according to methods well known by persons skilled in the art, when a murine antibody is known and available.

The tPA inhibitors useful to reduce edema in tissue surrounding blood vessels and other nascent tissue in which tPA caused or contributes to increasing permeability and leakage of fluid into these tissues can be determined using the methods described in the present invention. For example, evaluation of Evans Blue extravasation as a measure of tPA-induced BBB permeability and in situ tPA activity are useful to select other compounds that inhibit tPA directly by binding to tPA or antagonists that interfere with the binding of tPA to a receptor that induces an increase in vascular permeability. The selection of these compounds is based on a comparison of Evans Blue extravasation in wild-type normal brain in which a stroke has not been induced or wild-type brains in which a stroke has been induced with a stroke induced plus treatment with a potential inhibitor.

The present method delivers the tPA inhibitor to the subject via any approach that effectively will reach the tissue where the tPA is located. Pharmaceutical compositions containing the tPA inhibitor of the invention in combination with a pharmaceutically acceptable carrier may be administered parenterally, intrathecally, intracistemally, intravaginally, topically (as by powders, ointments, drops or transdermal patch), bucally, or as an oral or nasal spray (intranasally). By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intrarticular injection and infusion.

In a preferred embodiment, administration is intravenuously, intrathecally or via nasal administration (intranasally) so that it reaches the tissue. Particularly, preferred administration modes for delivery to vascular bed in the area of the blood brain barrier, is intrathecal or intranasal administration. As used herein, the term "intrathecal administration" or intrathecally is intended to include delivering a tPA inhibitor pharmaceutical formulation directly into the cerebrospinal fluid of a subject, by techniques including lateral cerebroventricular injection through a burrhole or cisternal into the cisterna magna or lumbar puncture into the lumbar regions or the like, as described, for example, in Lazorthes et al., ADVANCES IN DRUG DELIVERY SYSTEMS AND APPLICATIONS IN NEUROSURGERY, 143-192 and Omaya et al., *Cancer Drug Delivery,* 1: 169-179). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of a tPA inhibitor to any of the above mentioned sites can be achieved by direct injection of the tPA inhibitor or by the use of infusion pumps.

For injection, the tPA inhibitor formulation of the invention can be formulated in liquid solutions, preferably in physiologically compatible buffers such as Hank's solution or Ringer's solution. In addition, the tPA inhibitor formulation may be formulated in solid form and re-dissolved or suspended immediately prior to use. Lyophilized forms are also included. The injection can be, for example, in the form of a bolus injection or continuous infusion (e.g., using infusion pumps) of the tPA inhibitor formulation.

In one embodiment of the invention, said tPA inhibitor formulation is administered by lateral cerebro ventricular injection into the brain of a subject in the inclusive period from the time of the injury for several hours or even days if necessary to reduce the edema in the tissue. The injection can be made, for example, through a burr hole made in the subject's skull. In another embodiment, the encapsulated tPA inhibitor is administered through a surgically inserted shunt into the cerebral ventricle of a subject in the inclusive period from the time of the injury for several hours or even days if necessary to reduce the edema in the tissue. For example, the injection can be made into the lateral ventricles, which are larger, even though injection into the third and fourth smaller ventricles can also be made.

In yet another embodiment, the tPA inhibitor formulation is administered by injection into the cisterna magna, or lumbar area of a subject in the inclusive period from the time of the injury for several hours or even days if necessary to reduce the edema in the tissue.

In a further embodiment, intranasal administration has been verified as a useful mode of administration via a direct nose-brain pathway (Pietrowsky et al., *Biol. Psychiatry,* 39(5):332-340 (1996), and the tPA inhibitor formulation can be administered in this manner.

The tPA inhibitor is also suitably administered by sustained-release systems. A tPA inhibitor formulation may further be included in a fibrin sealant as described in U.S. Pat. No. 6,117,425. Other suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547-556 (1983)), poly (2-hydroxyethyl methacrylate) (R. Langer et al., *J. Biomed. Mater. Res.* 15:167-277 (1981), and R. Langer, *Chem. Tech.* 12:98-105 (1982)), ethylene vinyl acetate (R. Langer et al., Id.) or poly-D-(−)-3-hydroxybutyric acid (EP 133,988). Sustained-release tPA inhibitor compositions also include lipid entrapped tPA inhibitors, such as liposomes containing tPA inhibitors which are prepared by methods known per se: DE 3,218,121; Epstein et al., *Proc. Natl. Acad Sci. (USA)* 82:3688-3692 (1985); Hwang et al., *Proc. Natl. Acad. Sci. (USA)* 77:40304034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type—which the lipid content is greater than about 30 mol. percent cholesterol, the selected proportion being adjusted for the optimal tPA inhibitor therapy.

For parenteral administration, in one embodiment, the tPA inhibitor is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the tPA inhibitor (and, optionally, any cofactor which may enhance its activity) uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient or compatible with the cerebral spinal fluid. Examples of such carrier vehicles include water, saline, Ringer's solution, and dextrose solution. Non-aqueous vehicles such as fixed oils and ethyl oleate are also useful herein; as well as liposomes.

A pharmaceutical preparation to be administered orally or parenterally can be obtained by using the compound of the present invention with a carrier, an excipient, a diluent and other additives. The carrier suitably contains minor amounts of additives such as substances that enhance isotonicity and chemical stability. Such materials are non-toxic to recipients at the dosages and concentrations employed; and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamnic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

Further, preparations of the tPA inhibitors of the present invention can pass the blood-brain barrier (*J. Lipid Res.*, 32, 713-722 (1991)) so that effectiveness to cerebral vascular tissue in which the tPA is increasing the permeability as causing the edema. The liposome preparation can be prepared according to a known liposome preparation method. C. G. Knight, LIPOSOMES: FROM PHYSICAL STRUCTURE TO THERAPEUTIC APPLICATIONS, pages 51-82, Elsevier, Amsterdam, 1981; *Proc. Natl. Acad. Sci., USA*, 75, 4194 (1978). Further, by making the compound of the present invention to be carried on liposome having, on a membrane thereof, a glucose residue, a tyrosine residue, a mannose residue or sulfatide obtained by adding 5-octylglucoside, L-tyrosin-7-amido-4-methylcoumarin, phenylaminomannoside or sulfatide as a membrane-forming substance in addition to the above amphipathic substance and additives, the liposome can be made to permeate a blood-brain barrier easily. As to a method itself, see Japanese Provisional Patent Publication No. 69332/1992.

EXPERIMENTS

Methods

Animal Preparation and Surgery

Animal Models: MCAO was induced in adult Sprague-Dawley rats weighting 350-400 g as described (Yepes et al. *Blood* 96, 569-576 (2000)), or in mice as described (Nagai, et al. *Circulation* 99, 2440-2444 (1999)). Murine strains were tPA$^{-/-}$ or Plg$^{-/-}$ backcrossed at least 7 generations into C57BL/6J (Netzel-Arnett,S. et al., *J. Biol. Chem.* 277, 45154-45161 (2002)) or their wild type controls (C57BL/6J) or MMP-9$^{-/-}$ (Vu, T. H. et al., *Cell* 93, 411-422 (1998)) on a pure 129S6/SvEv background (Betsuyaku, T., et al.i, *I Am.J.Respir.Cell.Mol.Biol.* 20, 1303-1309 (1999) (a generous gift from Drs. Michael Shipley and Robert Senior from Washington University School of Medicine, St. Louis, Mo.) or their wild type 129S6/SvEv controls (Taconic). Treatment of rats with neuroserpin following MCAO was performed immediately following MCAO by intracortical injection with 20 µl of either PBS, or 16 µM neuroserpin as described (Yepes, supra (2000). Treatment of mice with neuroserpin following MCAO was performed by intraventricular injection of 2.5 µl of 16 µM neuroserpin at bregma-2, medial-lateral: 0 and dorso-ventral: 2 (Paxinos, G. & Franklin, K. B. J., *The Mouse Brain in Sterotaxic Coordinates*, Academic Press Inc., San Diego, Calif. (2001).

Analysis of Vascular Permeability Using Evans Blue Extravasation

Changes in vascular permeability following MCAO in mice were determined by I.V. injection of Evans Blue (4 ml/Kg IV; Sigma, St. Louis Mo.), 2% in saline, immediately after MCAO followed six hours later by transcardiac perfusion. The brains were then removed, divided into ipsilateral and contralateral hemispheres, weighed, homogenized in 400 µl of N,N-Dimethylformamide and centrifuged at 21,000 g for 30 minutes. Evans Blue was quantified from the absorbance at 620 nm of each supernatant minus the background calculated from the baseline absorbance between 500 and 740 nm and divided by the wet weight of each hemisphere.

To determine vascular permeability following intraventricular injection of tPA, anesthetized animals were placed on a stereotactic frame and injected with 2.5 µl of either tPA (60 µg/ml) or a combination of tPA and RAP (700 µg/ml) at coordinates bregma-2, medial-lateral: 0 and dorso-ventral: 2 (Paxinos, G. &Franklin, K. B. J.,supra), followed by the I.V. injection of 2% Evans Blue. A different group of animals was first injected I.P. with 100 µl of MK-801 (2 mg/ml) 1 hour before intraventricular injection of tPA. For all groups, brains were extracted after one hour and Evans Blue extravasation was analyzed as above except that brains were not separated into hemispheres and were extracted in 800 µl. Statistical analyses for all quantitative experiments were performed with the Wilcoxon two sample test and p values 0.05 or less were considered significant.

Microscopy and In Situ Proteinase Activity and Evans Blue Detection

Mice were intracardially perfused with a mixture of PBS and 10% paraformaldehyde 1 and 6 hours after MCAO. The brains were removed, frozen in OCT and stored at −70 C°. For analysis of tPA activity, 5 µm cryostat sections were treated as described elsewhere (Yepes et al., *J.Clin.Invest.* 109, 1571-1578 (2002)). To study Evans Blue extravasation, brain section were observed under fluorescent microscope with TRITC filter.

EXAMPLE 1

Study of Blood Brain Barrier Permeability Following Cerebral Ischemia

To evaluate the effect of tPA and MMP-9 on BBB opening following MCAO, mice underwent MCAO followed by intravenous injection of Evans Blue as described in the Methods sections. Brains were extracted 6 hours later. Evans Blue extravasation in wt, tPA−/−, plg−/− and MMP-9−/− mice 6 hours after MCAO were evaluated (FIG. 1A). The compilation of the data (FIG. 1B) shows a large increase in BBB permeability in wt animals 6 hours after MCAO that was significantly decreased in tPA −/− mice, suggesting a direct link between tPA activity and BBB opening in cerebral ischemia. In contrast, no significant difference was observed in ischemia-induced Evans Blue leakage between wild type and plg−/− animals, suggesting that tPA induces opening of the BBB by a plasminogen independent mechanism. Moreover, MMP-9−/− deficient animals exhibited a BBB opening comparable to WT animals, suggesting that at least in early stages of cerebral ischemia and in the absence of reperfusion, the opening of the blood brain barrier is mediated by tPA and that this event is independent of MMP-9 activity. These data demonstrate that tPA is required for BBB opening following cerebral ischemia and suggests the local action of tPA directly on the BBB.

MMP-9 activity in brain extracts following cerebral ischemia was measured via zymographic assay of brain extracts. For this analysis gelatin zymographic assays of rat brains were performed 6 hours after MCAO with and without injection of the tPA inhibitor neuroserpin directly into the ischemic area. These results revealed a marked decrease in MMP-9 activity in neuroserpin-treated animals compared to animals treated with PBS only. Treatment of brain extracts with neuroserpin ex vivo indicated that as expected neuroserpin did not directly inhibit MMP-9, and therefore suggests that the inhibition of tPA activity indirectly blocks the rise in MMP-9 activity that occurs after ischemic stroke. To confirm that this result was due to the inhibition of tPA activity in the neuroserpin treated animals and was not due to the effect of neuroserpin on another unidentified protease, the MMP-9 activity was analyzed in tPA$^{-/-}$ and Plg$^{-/-}$ mice 6 hours after MCAO. These data demonstrated that compared to wt animals, tPA$^{-/-}$ mice showed a marked decrease in MMP-9 activity, whereas Plg$^{-/-}$ mice did not. Quantitative PCR analysis of brain tissue from normal wt mice and from the ischemic and non ischemic hemispheres of wt mice 6 hours after MCAO indicated that there was no local increase in MMP-9 gene expression following cerebral ischemia. Likewise, treatment of either non-ischemic brain extracts or purified human proMMP-9 with tPA demonstrated that tPA had no affect on the MMP-9 in either case, indicating that tPA was not acting directly on MMP-9. Together these results suggest that there is a Plg-independent link between tPA and MMP-9 following cerebral ischemia that is not due to the local action of tPA on either MMP-9 protein or gene expression. Instead it may be that the rise in MMP-9 was due to the increased passage of free MMP-9 from the blood into the brain through the BBB or as a component of invasive neutrophils. None of the above data is shown.

EXAMPLE 2

Figure 2:
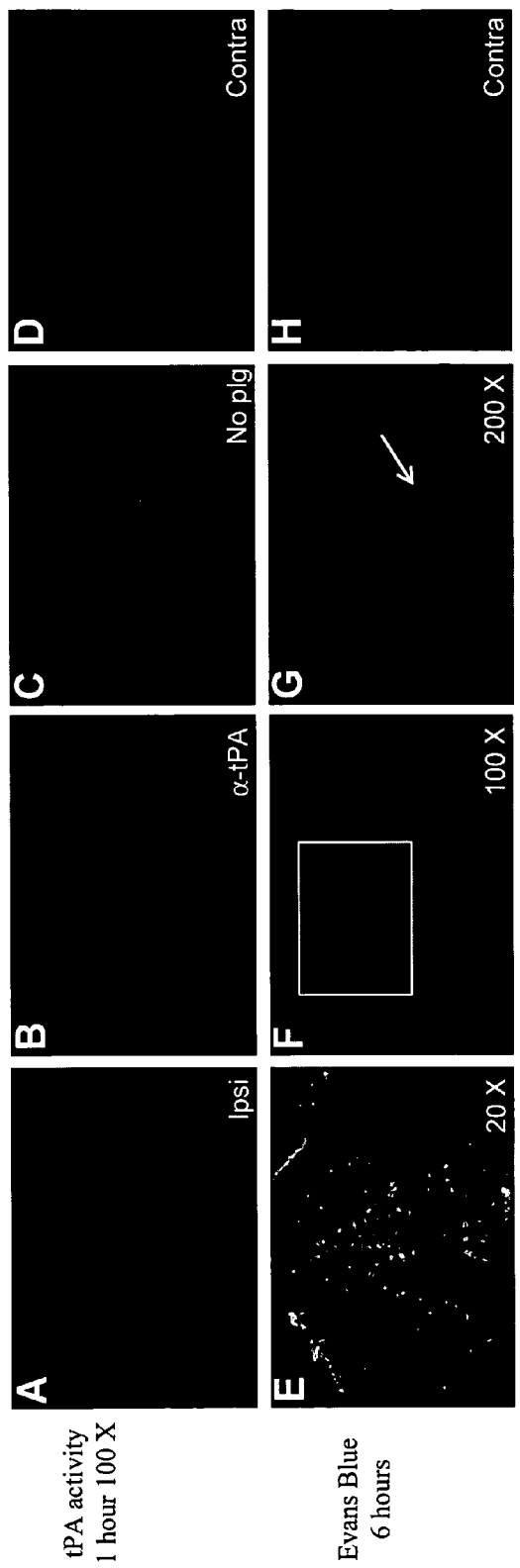
FIG. 2 shows the temporal and spatial correlation between tPA activity and vascular permeability following MCAO in wild-type (C57BL/6J) mice. Panels A to D show tPA activity by in situ zymography and cell nuclei (DAPI) 1 hour after MCAO. Panel A shows the proteinase activity surrounding a blood vessel adjacent to the necrotic area. Panels B and C show the same blood vessel described in panel A, but after either the addition of anti-tPA antibodies (B) or the absence of plasminogen (C). Panel D shows the background tPA activity surrounding a blood vessel in a corresponding area in the contralateral hemisphere from the same section shown in panel A. Magnification 100×. Panels E to H show tPA activity by in situ zymography and cell nuclei (DAPI) 6 hours after MCAO. Panel E shows a low magnification Evans Blue extravasation in the entire ischemic area 6 hours after MCAO. Panel F shows Evans Blue extravasation from a blood vessel located in the area adjacent to the ischemic area similar to panel A. Panel G shows a 200× magnification of the box in panel F. The arrow indicates the point of Evans Blue leakage outside of the internal elastic lamina of the vessel. Panel H shows Evans Blue adhering to the vessel wall but no extravasation in a blood vessel in the same brain section as seen in panels F and G but located in the contralateral hemisphere.

Temporal and Spatial Relationship Between tPA Activity and Vascular Permeabilty Following Cerebral Ischemia To further test this hypothesis, the temporal and spatial relationship between tPA activity and Evans Blue leakage following MCAO was analyzed. The results show that as early as one hour following MCAO, there was an increase in tPA activity surrounding the blood vessels adjacent to the necrotic core (ischemic penumbra), and that this activity preceded an increase in vascular permeability in the same area 6 hours later. FIG. 2, panels A-H, show the results and demonstrate a direct relationship between tPA activity and increased permeability of the BBB, and suggests a model, in which following cerebral ischemia, there is an increase in tPA activity within the interstitial tissue closely surrounding the cerebral vessels with subsequent opening of the blood brain barrier in these vessels.

In contrast, ischemia-induced Evans Blue dye leakage was not reduced in either, uPA$^{-/-}$ (data not shown) and Plg$^{-/-}$ animals, indicating that tPA induces opening of the BBB by a Plg-independent mechanism. Moreover, MMP-9$^{-/-}$-deficient animals also exhibited Evans Blue dye extravasation comparable to wt animals, demonstrating that at least in early stages of cerebral ischemia the opening of the blood brain barrier is mediated by tPA and is independent of MMP-9. To confirm that the effect of neuroserpin on Evans Blue dye leakage was specific and was not simply due to the injection or was an effect of the vehicle, a dose-response of neuroserpin was performed. These data (not shown) indicate that Evans Blue dye leakage decreases as the concentration of neuroserpin increases up to 4 µM, and saturates at a point where higher concentrations (up to 16 µM) of neuroserpin do not have any additional effect.

EXAMPLE 3

Quantitative Analysis of Fluid Extravasation From Brain Extracts

Figure 3:
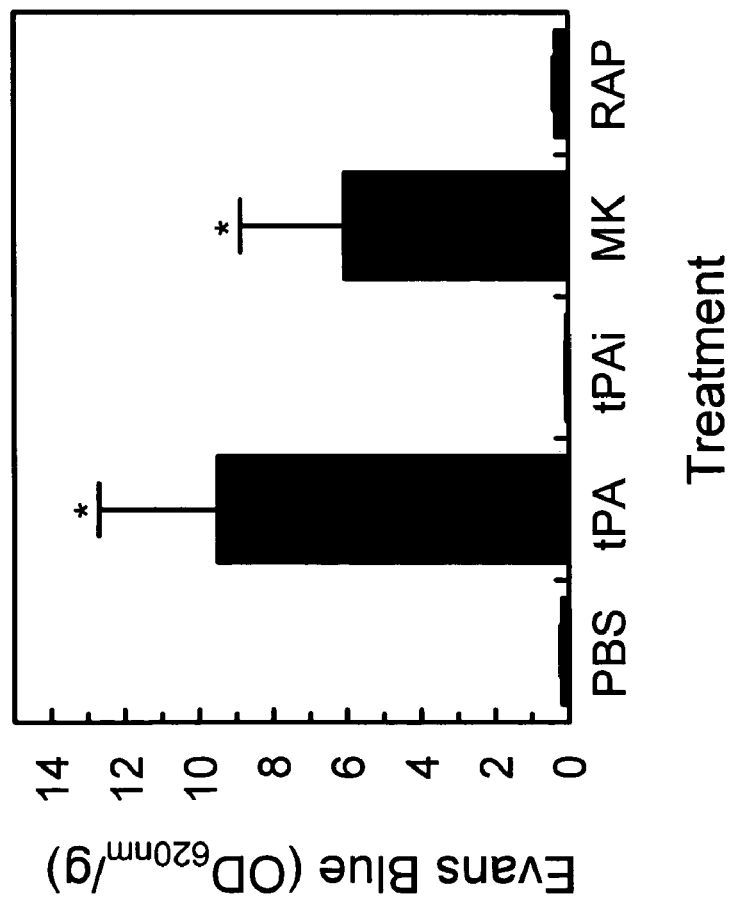
FIG. 3 shows the quantitative analysis of Evans Blue extravasation from brain extracts 1 hour after intraventricular injection of 2.5 μl of either PBS (PBS), tPA (60 μg/ml) (tPA), proteolytically inactive tPA (60 μg/ml) (tPAi), a combination of intraperitoneal MK-801 (an antagonist of NMDA (N-methyl-D-aspartate) receptor) (2 mg/ml) and intraventricular tPA (60 μg/ml), or a combination of intraventricular tPA and RAP (60 μg/ml and 700 μg/ml, respectively). The results represent the absorbance at 620 nm substracted for background absorbance and calculated as percentage per weight of tissue as described herein. For each condition n=6 except for tPAi where n=4 and the * indicates p<0.01 vs. etiher PBS, tPAi or tPA with RAP.

To study whether tPA alone, in the absence of cerebral ischemia, is sufficient to cause opening of the blood brain barrier, Evans blue leakage was studied 1 hour after the intraventricular injection of 150 ng of tPA. This analysis demonstrated that there was a significant increase in vascular permeability following the intraventricular injection of tPA in the absence of cerebral ischemia (FIG. 3). Further, this effect was dose-dependent, with an estimated $ED_{50}$ of approximately 425 nM tPA (data not shown). Moreover, no leakage of Evans blue was observed in the presence of inactive tPA. These results indicate that tPA within the CNS is not only necessary, but is sufficient to produce opening of the blood brain barrier, and that the tPA must be proteolytically active.

Taken all together, the results provided herein demonstrate that following cerebral ischemia, tPA opens the BBB by a proteolytic mechanism that is plasminogen-independent. Previous reports have suggested that tPA can interact with two different receptors known to be present within the CNS, the NR-1 sub-unit of the NMDA receptor (Nicole. et al. *Nat. Med.* 7, 59-64 (2001)), and LRP, a member of the LDL receptor family (Bu et al. *Proc. Natl. Acad. Sci. U. S. A* 89, 7427-7431 (1992)).

To see if the observed increase in BBB permeability was due to the direct action of tPA on the NR1 sub-unit of the NMDA receptor, the leakage of Evans blue was evaluated following the intraventricular injection of tPA in animals pretreated one hour before with an intraperitoneal injection of the NMDA receptor antagonist MK-801. These experiments indicate that there was no significant decrease in the tPA-induced increase in BBB permeability in MK-801-treated animals, suggesting that the observed increased in BBB permeability following treatment with tPA was not mediated by the NMDA receptor.

To investigate whether LRP or another member of the LDL receptor family mediates the tPA opening of the BBB, Evans blue extravasation was evaluated following the intraventricular co-injection of tPA together with a 20-fold molar excess of the LDL receptor family antagonist, receptor associated protein (RAP) (Bu et al. *Curr. Opin. Lipidol.* 9, 149-155 (1998)). These studies demonstrate that there was a marked decrease in tPA-induced BBB permeability when RAP was administered simultaneously with tPA, suggesting that the action of tPA on the BBB is mediated by LRP or some other member of the LDL receptor family. To determine if tPA was acting specifically through LRP, Evans Blue extravasation was determined when tPA was co-administered with anti-LRP antibodies. These results demonstrated that antibodies against LRP completely blocked this effect of tPA, confirming the role of LRP in this process.

Taken together, the data presented here suggest a model for tPA regulation of vascular permeability that requires tPA activity but is both Plg- and MMP-9-independent. In the case of cerebral ischemia, it appears as though an early rise in tPA activity in the sub-vascular tissue, possibly released from activated microglial cells (Chia-Jen Siao, et al., *The J. Neuroscience* 23, 3224-3242 (2003)), results in the association of this tPA with LRP or a related receptor possibly located on the perivascular smooth muscle cells or pericytes. Interestingly, previous studies have suggested that LRP can mediate intracellular signaling both in the CNS where it modulates LTP (Zhuo, M. et al., *J. Neurosci.* 20, 542-549 (2000)). and in vascular smooth muscle cells where it regulates smooth muscle cell proliferation (Boucher et al. *Science* 300, 329-332 (2003)). Thus, it is likely that the association of tPA with LRP induces an increase in vascular permeability via a specific cell signaling event, and if the signal persists or is too robust, then this increased permeability leads to opening of the BBB and vasogenic edema. TPA may also promote vasogenic edema in other neurological pathologies such as subarachnoid hemorrhage where the presence of blood-born tPA in the sub-vascular tissue may promote increased vascular permeability, with subsequent cerebral edema. Likewise, this process may also play a role in vascular permeability outside of the CNS, since tPA antigen has been observed in the sympathetic axons innervating the smooth muscle in the walls of peripheral vessels (Jiang, et al. *Microvasc. Res.* 64, 438-447 (2002)), which are also know to express significant levels of LRP (Boucher et al. *Science* 300, 329-332 (2003), Llorente-Cortes et al. *Arterioscler. Thromb. Vasc. Biol.* 20, 1572-1579 (2000)). Thus, these results imply a new Plg-independent role for tPA as a potent but previously unrecognized regulator of vascular permeability and raise significant questions about the safety of recombinant tPA for the treatment of acute stroke patients.

All of the publications and patent documents cited herein are incorporated in their entirety by reference in support of the present disclosure.

We claim:

1. A method of reducing vascular permeability in tissue comprising the step of administering to a subject in need thereof a therapeutically effective amount of a tissue plasminogen activator (tPA) inhibitor of tPA interaction with a low density lipoprotein (LDL) receptor-related protein (LRP) sufficient to reduce the vascular permeability increasing activity of the tPA.

2. The method of claim 1, wherein said activity of tPA which increases vascular permeability is independent of its interaction with plasminogen conversion to plasmin.

3. The method of claim 2, wherein said increase in vascular permeability in the tissue results in edema in the tissue.

4. The method of claim 3, wherein said edema in the tissue is a result of an injury, a condition, a disease or a disorder of said subject.

5. The method of claim 4, wherein said injury, condition, disease or disorder is selected from the group consisting of a head trauma, pulmonary edema, peripheral vascular disease, ischemic stroke, cystitis, pancreatitis, brain tumor, spinal cord tumor, spinal cord trauma, polymyositis, dermatomyositis, pulmonary embolism, enterocolitis, hepatic congestion, cerebral venous thrombosis, intracerebral hemorrhage, post-surgical manipulation, nephritis and glomerulonephritis, brain injury and sepsis.

6. The method of claim 4, wherein said edema is associated with an injury, trauma, disorder or disease to the brain in which increased vascular permeability results in the loss of the integrity of the blood brain barrier.

7. The method of claim 2, wherein said tPA inhibitor is administered intravenuously, intrathecally or via nasal administration so that it reaches the tissue.

8. The method of claim 7, wherein said tPA inhibitor is associated with lipids to facilitate delivery to the tissue.

9. The method of claim 2, wherein said tPA inhibitor is administered simultaneously with tPA and in a therapeutically effective amount to inhibit the vascular permeability increasing activity of tPA.

10. The method of claim 2, wherein said tPA inhibitor decreases the tPA-induced blood brain barrier permeability in said subject.

11. The method of claim 2, wherein said tPA inhibitor inhibits the binding of tPA to a low-density lipoprotein (LDL) receptor family protein.

12. The method of claim 11, wherein said LDL receptor family protein comprises a low-density lipoprotein receptor-related protein (LRP).

13. The method of claim 12, wherein said tPA inhibitor is the receptor associate protein (RAP).

14. The method of claim 2, wherein said tPA inhibitor inhibits the proteolytic activity of tPA.

15. The method of claim 14, wherein said tPA inhibitor is a proteinase inhibitor.

16. The method of claim 14, wherein said tPA inhibitor is neuroserpin, mutant neuroserpin, wild-type PAl-1, mutant PAl-I or an antibody that binds to tPA.

17. The method of claim 2, wherein said tPA inhibitor is neuroserpin, mutant neuroserpin, wild-type PAl-1, mutant PAl-1, an antibody that binds to tPA, an antibody that binds to the low-density lipoprotein (LDL) receptor or a low-density lipoprotein (LDL) receptor family antagonist.

18. The method of claim 17, wherein said LDL receptor family antagonist is the receptor associate protein (RAP).

* * * * *